United States Patent [19]
Schilling, Jr. et al.

[11] Patent Number: 5,939,574
[45] Date of Patent: Aug. 17, 1999

[54] AMINOSILOXANES WITH 4-AMINO-3,3-DIALKYLBUTYL GROUPS

[75] Inventors: Curtis L. Schilling, Jr., Marietta, Ohio; Anna Czech, Cortlandt Manor, N.Y.; Robert E. Sheridan, Marietta, Ohio; Gerald J. Murphy, Hopewell Junction, N.Y.

[73] Assignee: Witco Corporation, Greenwich, Conn.

[21] Appl. No.: 09/115,284

[22] Filed: Jul. 14, 1998

Related U.S. Application Data

[63] Continuation-in-part of application No. 08/834,633, Apr. 14, 1997, Pat. No. 5,856,544
[60] Provisional application No. 60/015,991, Apr. 15, 1996.

[51] Int. Cl.⁶ .................................................... C07F 7/10
[52] U.S. Cl. ...................... 556/425; 556/413; 556/425
[58] Field of Search ..................................... 556/415, 425, 556/413

[56] References Cited

U.S. PATENT DOCUMENTS

| | | |
|---|---|---|
| 3,033,815 | 5/1962 | Pike et al. . |
| 3,146,250 | 8/1964 | Speier et al. . |
| 3,661,964 | 5/1972 | Griffiths et al. ........................ 556/425 |
| 4,098,701 | 7/1978 | Burrill et al. . |
| 4,152,346 | 5/1979 | Seiler et al. ............................ 556/413 |
| 4,247,592 | 1/1981 | Kalinowski . |
| 4,651,577 | 3/1987 | Jo Lane et al. . |
| 5,039,738 | 8/1991 | Czech . |
| 5,073,275 | 12/1991 | Ona et al. . |
| 5,354,880 | 10/1994 | Pepe et al. . |
| 5,391,400 | 2/1995 | Yang . |
| 5,486,634 | 1/1996 | Hahn et al. ............................. 556/425 |
| 5,496,401 | 3/1996 | Yang . |
| 5,567,752 | 10/1996 | Stein et al. ......................... 556/425 X |

FOREIGN PATENT DOCUMENTS

| | | |
|---|---|---|
| 0577039 | 1/1994 | European Pat. Off. . |
| 0692567 | 1/1996 | European Pat. Off. . |

OTHER PUBLICATIONS

Lautenschlager H.J. et al. "Struktur–Wirkungsbeziehung Aminofunktioneller Siliconweichmachungsmittel" Textil Praxis International, vol. 47, No. 5, May 1, 1992, pages.

*Primary Examiner*—Paul F. Shaver
*Attorney, Agent, or Firm*—Edward K. Welch, II; Andrew S. Reiskind; Timothy X. Witkowski

[57] ABSTRACT

Aminosiloxanes bearing 4-amino-3,3-dialkylbutyl substituents are prepared by a multistep process including addition of 2,2-dialkylacetonitrile to vinylic siloxanes, hydrogenation of the nitrile adducts so formed to yield 4-amino-3,3-dialkylbutyl siloxanes, and optional equilibration of the latter with other siloxane sources, to form aminosiloxanes, which are useful for the treatment of textiles and fabrics and for the preparation of siloxane-containing block copolymers.

20 Claims, No Drawings

AMINOSILOXANES WITH 4-AMINO-3,3-DIALKYLBUTYL GROUPS

This application is a continuation-in-part of U.S. application Ser. No. 08/834,633, filed on Apr. 14, 1997 now U.S. Pat No. 5,856,544, which claims priority to provisional application Ser. No. 60/015,991, filed Apr. 15, 1996.

FIELD OF THE INVENTION

The present invention relates to novel aminosiloxanes with 4-amino-3,3-dialkylbutyl groups, to their aminosiloxane starting materials and their preparation, and to the cyanoalkylsiloxanes used to make the aminosiloxane starting materials and their preparation. Aminosiloxanes with 4-amino-3,3-dialkylbutyl groups are useful in the treatment of textiles and fabrics, and those aminosiloxanes endblocked with 4-amino-3,3-dialkylbutyl groups are useful in the preparation of siloxane-containing block copolymers with surface-active properties.

BACKGROUND OF THE INVENTION

There has been a continuing need in the industry for aminopolysiloxanes which are useful for treating textiles and fabrics without discoloration or yellowing of such textiles and fabrics, and for aminoalkyl-endblocked siloxanes which are useful in the preparation of siloxane-containing block copolymers with surface-active properties. There has also been a continuing need for simpler processes for making said aminosiloxanes and aminoalkyl-endblocked siloxanes, particularly regarding the starting materials from which they are prepared.

The preparation of aminoalkylsilanes containing hindered 4-amino-3,3-dialkylbutyl groups is described in U.S. Pat. No. 5,354,880, which is incorporated herein by reference. The conversion of said aminoalkylsilanes to aminosiloxanes with 4-amino-3,3-dialkylbutyl groups is described in copending U.S. application Ser. No. 08/834,633, which is incorporated herein by reference. Prior methods for the preparation of siloxanes with 4-amino-3,3-dialkylbutyl groups have involved the preparation of dialkoxy 4-amino-3,3-dialkylbutylsilanes and their hydrolyses to aminosiloxane intermediates which were equilibrated with hexamethyldisiloxane, octamethylcyclotetrasiloxane, or other reactants to form the final aminosiloxanes with 4-amino-3,3-dialkylbutyl groups and a majority of dimethylsiloxane units. The dialkoxy 4-amino-3,3-dimethylbutylsilanes were prepared by a sequence of reactions beginning with the base-catalyzed addition of isobutyronitrile to a vinyl alkoxy silane, and subsequent hydrogenation of the nitrile adduct to the corresponding aminoalkylsilane.

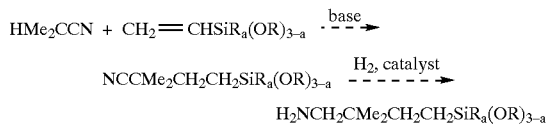

SUMMARY OF THE INVENTION

It has been discovered that there is an alternate route for the preparation of aminosiloxanes with 4-amino-3,3-dialkylbutyl groups not involving the preparation of the corresponding aminoalkylsilane intermediates, with such route being particularly applicable to the preparation of aminosiloxanes endblocked with 4-amino-3,3-dialkylbutyl groups. The alternate route involves the addition of a 2,2-dialkylacetonitrile to a vinylic siloxane, to produce a 3-cyano-3,3-dialkylpropyl siloxane, subsequent hydrogenation of this nitrile adduct to 4-amino-3,3-dialkylbutyl siloxane, and optionally, equilibration with dialkylsiloxane sources to form the aminosiloxane with 4-amino-3,3-dialkylbutyl groups.

DETAILED DESCRIPTION OF THE INVENTION

It has been discovered that the base-catalyzed addition of 2,2-dialkyl-acetonitrile can be effected efficiently with vinylic siloxanes, including polyvinylic siloxanes, obviating the need to prepare the corresponding monomeric precursors, i.e., the silanes. The nitrile addition reaction is particularly effective with 1,3-divinyltetramethyldisiloxane, providing a high yield of 1,3-bis(3-cyano-3-alkylbutyl)tetramethyldisiloxane, which can be hydrogenated to the endblocker, 1,3-bis(4-amino-3,3-dialkylbutyl)tetramethyldisiloxane, as shown below, where, for example, alkyl is a methyl group.

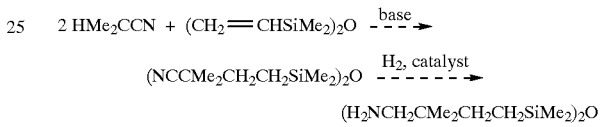

The efficient base-catalyzed addition of 2,2-dialkylacetonitrile to vinylic siloxanes, particularly including 1,3-divinyltetramethyldisiloxane, is surprising in that cleavage of the siloxane bonds and neutralization of the base catalyst does not occur. While similar addition of nitiles to other vinylic siloxanes, including polyvinylic siloxanes, can be performed, it is recognized that the degree of reaction (efficiency) may be lower with other vinylic siloxanes, and that the degree of siloxane bond cleavage (rearrangement, equilibration) may be higher. A reaction between the nitrile and a polyvinylic siloxane thus may yield products with residual, unreacted vinyl groups. When the cyano groups present subsequently are hydrogenated to aminoalkyl groups, the residual vinyl groups will be converted to unreactive ethyl groups. Thus, an 4-amino-3,3-dialkylbutyl siloxane is produced.

If a siloxane of longer length than a disiloxane is desired, the disiloxane may be equilibrated with any source of dialkylsiloxane groups, particularly dimethylsiloxane groups, to yield the corresponding endblocked siloxanes. Such equilibration may be conducted on the vinyl endblocked disiloxane or on the amino-endblocked siloxane, preferably the latter, because of the aforementioned rearrangement, which equilibration may be exemplified as:

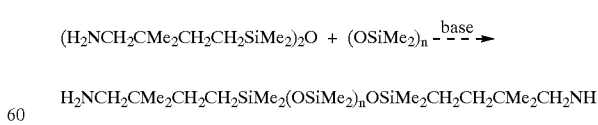

These siloxanes, being specifically bifunctional with regard to primary amine functionality, are useful in the preparation of siloxane-containing block copolymers through reactions with bifunctional polymers or monomers endblocked with groups reactive with primary amines (e.g., epoxy, see U.S. patent application Ser. No. 08/810,408 which is incorporated herein by reference). Siloxane-containing block copolymers are known in the art to be surface-active agents, as in the preparation of polyurethane foams.

The nitrile compound may have the formula $HCR^1{}_2CN$, wherein $R^1$ is an alkyl group of 1 to 6 carbon atoms. Isobutyronitrile is preferred.

The base used to catalyze the addition of the nitrile compound to the vinylic siloxane may be selected from the group of: (a) an alkali metal (sodium, potassium, lithium and cesium), (b) an alkali metal alkoxide such as sodium or potassium methoxide, (c) an alkali metal amide such as sodium amide, (d) an alkali meal hydride such as sodium hydride, or (e) mixtures thereof. Of this group, sodium metal is preferred and is employed to minimize undesirable side reactions. The concentration of base may be from 0.001 to more than 10.0 mole percent relative to the nitrile compound, and is preferably from 0.03 to 3.0 mole percent. After reaction, the base may be neutralized with a protic acid, such a acetic acid.

The vinylic siloxane is one having at least one unit of —OSiMe(—CH=CH$_2$)— and may be linear, cyclic or branched, though it is preferred to start with a cyclic siloxane or a vinyl endblocked disiloxane and equilibrate into said siloxanes additional siloxy units. The vinylic siloxane may be selected from the group of monovinyl siloxanes such as vinylpentamethyldisiloxane, 3-vinyl-1,1,1,3,5,5,5-heptamethyltrisiloxane, vinylheptamethylcyclotetra-siloxane, and the like; divinyl siloxanes such as 1,3-divinyltetramethyldisiloxane; or polyvinyl polysiloxanes such as 1,3,5-trivinyl-1,3,5-trimethylcyclotrisiloxane, 1,3,5,7-tetravinyl-1,3,5,7-tetramethylcyclotetrasiloxane, tris(vinyldimethylsiloxy) methylsilane or tetrakis(vinyldimethylsiloxy)-silane. Dimethylpolysiloxanes randomly substituted with vinyl groups also may be used, and said dimethylpolysiloxanes may contain monofunctional (Me$_3$SiO—), difunctional (—OSiMe$_2$—), trifunctional (MeSiO$_{3/2}$), or quaterfunctional orthosilicate (SiO$_{4/2}$) units. Cyclic dimethyl siloxanes have the formula $(OSiMe_2)_x(OSiMe(CH=CH_2)_y$ wherein x=1 to 10 and y=1 to 10, with x+y=3 to 12.

The resulting products, in addition to those previously disclosed in copending 08/834,633, may be end-blocked disiloxanes and modified cyclosiloxanes. These disiloxanes may be viewed as $R^2Me_2SiOSiMe_2R^2$ wherein $R^2$ is —CH$_2$CH$_2$C(R$^1$)$_2$CH$_2$NH$_2$ and $R^1$ is as above. A cyclic siloxane end product will have pendant $R^2$ groups. More specifically the cyclic amino siloxane may be viewed as $(SiOMe_2)_x(SiOMeR^2)_y$ wherein x and y are as above, though as readily understood in the art, other substituted siloxy units may be equilibrated into these cyclic siloxanes.

The nitrile addition reaction may be performed under a variety of conditions regarding temperature, pressure, and equipment, and optionally in the presence of an inert solvent, and should be performed under an inert atmosphere. One preferred set of operating conditions includes use of an agitated reactor at atmospheric pressure under a nitrogen atmosphere with no solvent, and a reaction temperature range of 100–150° C.

The hydrogenation reactions may be performed in a variety of ways known to those of ordinary skill in the art using an equally wide variety of catalysts, promoters, solvents, equipment, and reaction conditions. One preferred method includes use of a stirred autoclave, Raney Nickel catalyst, temperatures of 100–200° C., ammonia as a promoter, toluene as a solvent, and hydrogen pressures of 200–1000 psi (1.4 MPa–6.9 MPa).

The equilibration reactions typically are performed using various alkylsiloxy sources, including trimethylsiloxane sources, dimethylsiloxane sources, methylsiloxane sources, and orthosilicate sources and basic equilibration catalysts. Dimethylsiloxane sources, particularly octamethylcyclotetrasiloxane, and decamethylcyclopentasiloxane are preferred, and preferred basic catalysts are silanolates, particularly potassium silanolate and ammonium silanolate. Such equilibrations are well known in the art, being disclosed for example in U.S. Pat. Nos. 3,033,815 and 4,247,592, which are incorporated herein by reference.

EXAMPLES

All parts and percentages are by weight unless otherwise specified.

EXAMPLE 1

Preparation of Bis(3-cyano-3-methylbutyl) tetramethyldisiloxane To a 2 liter 4-necked flask fitted with an addition funnel, reflux condenser, thermometer, and magnetic stirring bar, and nitrogen flow valves, were charged 362.8 of isobutyronitrile and 2.33 grams of freshly cut sodium metal. The mixture was heated to reflux (105° C.) and addition of 430.9 grams of 1,3-divinyltetramethyldisiloxane completed over 4.5 hours, followed by heating at reflux for an additional 5 hours. After cooling and standing overnight, an additional 1.35 grams of sodium metal were added, and reflux continued until the pot temperature reached 150° C., where it was maintained for 2 hours, followed by cooling and standing overnight. The reaction mixture, which had solidified, was warmed to 110° C. and neutralized with 19.4 grams of acetic acid. The product was vacuum stripped to remove volatiles, producing 740 grams of a low melting tan solid, which was dissolved in 637 grams of toluene for ease in handling. Gas chromatographic analysis of the solid showed 92% purity of bis(3-cyano-3-methylbutyl)tetramethyldisiloxane.

EXAMPLE 2

Preparation of Bis(4-amino-3,3-dimethylbutyl) tetramethyldisiloxane To a 2 liter stirred autoclave were charged 654.8 grams of bis(3-cyano-3-methylbutyl) tetramethyldisiloxane dissolved in 636.7 grams of toluene, 24.7 grams (2 weight-%) of Raney Nickel slurried in 50 grams of toluene, and 110 grams of anhydrous ammonia. The system was sealed, pressured to 300 psi with hydrogen, and heated to 120° C. At temperature, the hydrogen pressure was adjusted to 700 psi and the reaction run for 21 hours. Infrared analysis of the reaction mixture after cooling, venting, and sampling, indicated the presence of unreacted nitrile groups. The hydrogenation step was repeated with additional ammonia, hydrogen, and nickel catalyst until the nitrile peak was absent from the infrared analysis. The crude reaction mixture was filtered, vacuum stripped, and vacuum distilled to yield bis(4-amino-3,3-dimethylbutyl) tetramethyldisiloxane.

EXAMPLE 3

Addition of Isobutyronitrile to 3-Vinyl-1,1,1,3,5,5,5-heptamethyltrisiloxane To a 100 milliliter 4-necked flask fitted as in Example 1 were charged 21.6 grams of isobutyronitrile, 23.1 grams of 3-vinyl-1,1,1,3,5,5,5-heptamethyltrisiloxane, and 0.25 grams (0.011 mole) of freshly cut sodium metal. The pot contents were slowly heated to reflux (109° C.) and held at that temperature for 4 hours. After cooling and standing overnight, an additional 0.1 gram of sodium metal was added, and reflux continued for 4 hours, followed by cooling and neutralization with 2.05 grams of acetic acid. Analysis of the crude reaction mixture prior to neutralization showed 38.5% isobutyronitrile, 9.1% hexamethyldisiloxane, 6.3% unreacted 3-vinyl- 1,1,1,3,5,5,5-heptamethyltrisiloxane, 25.8% 3-(3-cyano-3-methylbutyl)-1,1,1,3,5,5,5-heptamethyl-trisiloxane, 4.0% 3-(3-cyano-3-methylbutyl)-5-vinyl-1,1,1,3,5,7,7,7-octamethyltetrasiloxane, and 8.3% 3,5-bis(3-cyano-3-methylbutyl)-1,1,1,3,5,7,7,7-octamethyltetrasiloxane. This example shows that a lower yield with higher siloxane cleavage was obtained relative to Example 1.

EXAMPLE 4

Addition of Isobutyronitrile to 1,3,5-Trivinyl-1,3,5-trimethylcyclotrisiloxane To a 100 milliliter 4-necked flask fitted as in Example 1 were charged 25.7 grams of isobutyronitrile, and 0.3 gram of freshly cut sodium metal. The reactor contents were heated to reflux and 22.0 grams of 1,3,5-trivinyl-1,3,5-trimethylcyclotrisiloxane were added over a 30 minute period and reflux maintained for 1 hour. Cooling, reheating, and further addition of sodium occurred until the trisiloxane had been consumed, followed by neutralization with acetic acid (1.6 gram). Gas chromatographic analysis of the neutralized mixture showed that it contained cyclotrisiloxanes, cyclotetrasiloxanes, and cyclopentasiloxanes with varying degrees of 3-cyano-3-methylbutyl functionality. This example also shows a lower degree of reaction and a higher degree of siloxane bond cleavage (rearrangement/equilibration) than Example 1.

EXAMPLE 5

Preparation of 4-Amino-3,3-dimethylbutyl Endblocked Polysiloxanes

The aminopolysiloxanes set forth in Table 1 were prepared in a base catalyzed equilibration reaction using bis(4-amino-3,3-dimethylbutyl)-tetramethyldisiloxane or Aminopolysiloxane I, as a source of aminofunctionality, and octamethylcyclotetrasiloxane. Two different procedures were used:

Potassium silanolate catalyzed reactions were carried out at 140–150° C. for 6–8 hours followed by neutralization of the catalyst with acetic acid and vacuum stripping of the volatiles.

Ammonium silanolate catalyzed reaction were carried out at 90° C. for 6–8 hours followed by decomposition of the catalyst at 150° C. for 1–2 hours and vacuum stripping at 100° C. for 3 hours.

Charges for the preparation of the aminopolysiloxanes are summarized in Table 2.

TABLE 1

4-Amino-3,3-dimethylbutyl Modified Polysiloxanes

| Designation | Formula[1] | Viscosity (cps) | Amine Content (as wt % $NH_2$)[2] |
|---|---|---|---|
| Aminopolysiloxane I | $M^*D_{50}M^*$ | 200 | 0.77 |
| Aminopolysiloxane II | $M^*D_{250}M^*$ | 1750 | 0.18 |
| Aminopolysiloxane III | $M^*D_{250}M^*$ | 2100 | 0.19 |
| Aminopolysiloxane IV | $M^*D_{500}M^*$ | 5380 | 0.09 |

[1]$M^* = O_{1/2}SiMe_2(CH_3)_2CH_2CH_2C(CH_3)_2CH_2NH_2$; $D = OSi(CH_3)_2$;
[2]Amine content determined by titration

TABLE 2

Charges for the Preparation of 4-Amino-3,3-dimethylbutyl Modified Polysiloxanes

| Designation | Source of the Aminofunctionality/ Charge | Charge of Octamethyl-cyclotetrasiloxane | Catalyst/ Charge |
|---|---|---|---|
| Aminopolysiloxane I | Bis(4-amino-3,3-dimethylbutyl)-tetramethyldisiloxane 6.7 g | 74.0 g | Ammonium Silanolate 1.0 g |
| Aminopolysiloxane II | Aminopolysiloxane I 20.5 g | 74.0 g | Ammonium Silanolate 1.0 g |
| Aminopolysiloxane III | Bis(4-amino-3,3-dimethylbutyl)-tetramethyldisiloxane 6.7 g | 370.0 g | Potassium Silanolate 2.0 g |
| Aminopolysiloxane IV | Bis(4-amino-3,3-dimethylbutyl)-tetramethyldisiloxane 6.7 g | 740 g | Potassium Silanolate 4.0 g |

What is claim is:

1. A method for the preparation of nitrile adducts comprising reacting a nitrile compound $HCR^1{}_2CN$ wherein $R^1$ is an alkyl group of 1 to 6 carbon atoms with a vinylic siloxane in the presence of a base catalyst.

2. A method according to claim 1 additionally comprising: reducing the nitrile adduct with hydrogen in the presence of a hydrogenation catalyst to form a 4-amino-3, 3dialkylbutylsiloxane.

3. A method according to claim 2 additionally comprising equilibrating in the presence of a basic catalyst the 4-amino-3,3-dialkylbutylsiloxane with siloxane sources selected from the group consisting of trimethylsiloxane sources, dimethylsiloxane sources, methylsiloxane sources, and orthosilicate sources to produce 4-amino-3,3-dialkylbutyl siloxane containing siloxy units derived from said siloxane sources.

4. The method of claim 3 wherein the nitrile compound is isobutyronitrile, the vinylic siloxane is 1,3-divinyltetramethyldisiloxane, the nitrile adduct is 1,3-bis(3-cyano-3-methylbutyl)-tetramethyldisiloxane, the reduction product is 1,3-bis(4-amino-3,3-dimethylbutyl) tetramethyldisiloxane, and the equilibration product is an 4-amino-3,3-dimethylbutyl-enblocked polydimethylsiloxane.

5. The reaction product of claim 1.

6. The method of claim 1 wherein the nitrile is isobutyronitrile, and the vinylic siloxane is a methyl cyclosiloxane containing at least one vinyl substituent.

7. The method of claim 1 wherein the nitrile compound is isobutyronitrile and the vinylic siloxane is 3-vinyl-1,1,1,3,5,5,5-heptamethyltrisiloxane.

8. The method of claim 1 wherein the nitrile compound is isobutyronitrile and the vinylic siloxane is 1,3,5-trivinyl-1,3,5-trimethylcyclotrisiloxane.

9. The method of claim 1 wherein the base catalyst is selected from the group consisting of alkali metals, alkali metal alkoxides, alkali metal amides, alkali metal hydrides and mixtures thereof.

10. The method of claim 9 wherein the base catalyst is sodium metal.

11. The method of claim 3 wherein the basic catalyst used in the equilibration step is selected from the group consisting of potassium silanolate and ammonium silanolate.

12. A composition comprising a disiloxane end-blocked with a —$(CH_2)_2CR^1{}_2CH_2NH_2$ functionality wherein $R^1$ is a $C_1$–$C_6$ alkyl.

13. A composition comprising according to claim 12 which is 1,3-bis(4-amino-3,3-dimethylbutyl)tetramethyl disiloxane.

14. A siloxane comprising an aminocyclosiloxane having a pendant group of $(CH_2)_2CR^1{}_2CH_2NH_2$ wherein $R^1$ is a $C_1$–$C_6$ alkyl.

15. A siloxane according to claim 14 of the formula $(SiOMe_2)_x (SiOMeR^2)_y$ wherein $R^2$ is the pendant group x=0 to 10, y=1 to 10 and x+y=3 12.

16. A siloxane according to claim 15 wherein each $R^1$ is methyl.

17. A siloxane according to claim 15 wherein x=0 and y=4.

18. The equilibration product of claim 4.

19. A siloxane having a 3-cyano-3,3-dialkylpropyl pendant group.

20. The siloxane of claim 19 which is 1,3-bis(3-cyano-3-alkylbutyl)tetramethyldisiloxane.

* * * * *